(12) United States Patent
Ballerstadt et al.

(10) Patent No.: US 6,271,044 B1
(45) Date of Patent: Aug. 7, 2001

(54) METHOD AND KIT FOR DETECTING AN ANALYTE

(75) Inventors: Ralph Ballerstadt; Jerome S. Schultz, both of Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/073,784

(22) Filed: May 6, 1998

(51) Int. Cl.$^7$ .............................. A01N 1/02; C12Q 1/00; C12Q 1/70; G01N 33/53; G01N 33/543

(52) U.S. Cl. .......................... 436/518; 436/501; 436/514; 436/530; 436/533; 436/535; 436/536; 436/541; 436/529; 436/179; 436/808; 436/827; 435/2; 435/4; 435/5; 435/6; 435/7.1

(58) Field of Search ..................................... 436/501, 514, 436/518, 530, 533, 535, 536, 541, 827, 808, 179, 529; 435/2, 7.1, 4, 5, 6

(56) References Cited

U.S. PATENT DOCUMENTS

| | | |
|---|---|---|
| 3,482,943 | 12/1969 | Csizmas et al. . |
| 3,554,704 | 1/1971 | Ushakoff . |
| 3,674,438 | 7/1972 | Shen . |
| 3,692,491 | 9/1972 | Trentelman . |
| 3,720,760 | 3/1973 | Bennich et al. . |
| 3,725,004 | 4/1973 | Johnson et al. . |
| 3,892,841 | 7/1975 | Barg, Jr. . |
| 3,907,502 | 9/1975 | Brink . |
| 4,097,149 | 6/1978 | Aladjem et al. . |
| 4,104,026 | 8/1978 | Brooker et al. . |
| 4,162,208 | 7/1979 | Aladjem et al. . |
| 4,244,797 | 1/1981 | Aladjem et al. . |
| 4,366,241 | 12/1982 | Tom et al. . |
| 4,504,585 | * 3/1985 | Reynolds ............................. 436/518 |
| 4,517,288 | * 5/1985 | Giegel et al. ............................. 435/7 |
| 4,666,863 | 5/1987 | Edwards et al. . |
| 4,666,866 | 5/1987 | Krauth . |
| 4,711,839 | 12/1987 | Singhal . |
| 4,752,562 | * 6/1988 | Sheiman et al. ......................... 435/5 |
| 4,774,174 | 9/1988 | Giegel et al. . |

(List continued on next page.)

FOREIGN PATENT DOCUMENTS

19501159A1  7/1996  (DE) .

OTHER PUBLICATIONS

Ehwald et al., *Analytical Biochemistry*, 234, 1–8 (1996).
Goldstein et al., *Biochemistry*, 4(5), 876–883 (1965).
Ballerstadt et al., *Biosensors & Bioelectronics*, 9, 557–567 (1994).
Sumner et al., *Journal of Bacteriology*, 32 (2), 227–237 (1936).

*Primary Examiner*—Long V. Le
*Assistant Examiner*—Pensee T. Do
(74) *Attorney, Agent, or Firm*—Leydig, Voit & Mayer, Ltd.

(57) ABSTRACT

The present invention provides a viscometric method of detecting the presence or absence of an analyte in a solution. The method utilizes a dispersion of a conjugate and a receptor. The conjugate functions as an analog of the analyte, and the receptor can interact with both the analyte and the conjugate to change the viscosity of the dispersion. The test solution is introduced into an aliquot of the dispersion. Equivalent spots of the dispersion and the aliquot containing the analyte within the dispersion are then placed on a substrate such that the spots can spread upon the substrate. The presence of analyte in the test solution is detected by noting a change in the viscosity of the dispersion through a comparison of the spots. To facilitate the method, the invention provides a test kit comprising a conjugate comprising an analog of the analyte, a receptor binding the analog and the analyte, and a substrate upon which spots of liquid can spread.

10 Claims, 2 Drawing Sheets

U.S. PATENT DOCUMENTS

| | | |
|---|---|---|
| 4,778,751 | 10/1988 | El Shami et al. . |
| 4,861,711 * | 8/1989 | Freisen et al. ............... 436/514 |
| 4,956,275 | 9/1990 | Zuk et al. . |
| 4,959,307 * | 9/1990 | Olson ............................. 435/7 |
| 4,960,691 | 10/1990 | Gordon et al. . |
| 4,981,786 | 1/1991 | Dafforn et al. . |
| 4,999,285 | 3/1991 | Stiso . |
| 5,079,142 | 1/1992 | Coleman et al. . |
| 5,133,866 | 7/1992 | Kauvar . |
| 5,137,808 | 8/1992 | Ullman et al. . |
| 5,219,762 * | 6/1993 | Katamine et al. ............ 436/518 |
| 5,232,835 | 8/1993 | Litman et al. . |
| 5,260,193 | 11/1993 | Olson . |
| 5,401,633 * | 3/1995 | Sutton et al. ............... 435/6 |
| 5,494,639 * | 2/1996 | Grzegorzewski ............ 422/82.01 |
| 5,559,041 * | 9/1996 | Kang et al. ............... 436/518 |
| 5,602,040 * | 2/1997 | May et al. ............... 436/514 |
| 5,622,871 * | 4/1997 | May et al. ............... 436/514 |
| 5,624,809 | 4/1997 | Skold et al. . |
| 5,627,078 * | 5/1997 | Karl et al. ............... 436/512 |
| 5,698,395 * | 12/1997 | Ritterband et al. ............ 435/6 |
| 5,770,388 * | 6/1998 | Vorpahl ............... 435/7.25 |
| 5,837,551 * | 11/1998 | Ekins ............... 436/518 |

* cited by examiner

METHOD AND KIT FOR DETECTING AN ANALYTE

TECHNICAL FIELD OF THE INVENTION

The present invention relates to a method of detecting and measuring the concentration of an analyte.

BACKGROUND OF THE INVENTION

In many applications (e.g., medical diagnostic procedures, chemical analysis, etc.), it is desirable to detect the presence of and measure the concentration of a given analyte in a solution containing an unknown amount of the analyte. Depending upon the nature of the analyte, several protocols exist for acquiring such measurements. For example, where the analyte is immunogenic or comprises epitopes to extant antisera, immunological methods can be employed. Thus, for example, the techniques of immunoprecipitation, immunoconcentration, affinity column separation chromatography using antibodies, etc., can quantify the concentration of a given analyte within a solution.

More recently, a phenomenon for exploiting differential viscosity to measure analyte concentration was proposed (see, e.g., Ballerstadt et al., *Biosensors & Biolectronics*, 9, 557–67 (1994)). To exploit this viscometric affinity assay, several devices and concepts of miniaturized sensor systems have been developed (Id.; see also published German Patent application DE 19501159 Al). Additionally, there are hand-held devices for measuring the concentrations of certain analytes (e.g., glucose).

Many of the methods for measuring analyte concentration require relatively sophisticated equipment (e.g., centrifuges, affinity columns, cold storage facilities, etc.) or reagents (e.g., preparations of protein H, characterized monoclonal antibodies, etc.). Moreover, many of the devices available for measuring analyte concentration are relatively sophisticated electronic devices and are, therefore, too expensive for widespread application in many developing nations or otherwise unsuited for use under field conditions. Thus, despite these advances, there remains a need for simpler and more straightforward methods of detecting and measuring the concentration of such analytes. The present invention provides such a method.

BRIEF SUMMARY OF THE INVENTION

The present invention provides a viscometric method of detecting the presence or absence of an analyte in a solution. The method utilizes a dispersion of a conjugate and a receptor. The conjugate functions as an analog of the analyte, and the receptor can interact with both the analyte and the conjugate to change the viscosity of the dispersion. The test solution is introduced into an aliquot of the dispersion. Equivalent spots of the dispersion and the aliquot containing the analyte within the dispersion are then placed on a substrate such that the spots can spread upon the substrate. The presence of analyte in the test solution is detected by noting a change in the viscosity of the dispersion through a comparison of the spots. To facilitate the method, the invention provides a test kit comprising a conjugate comprising an analog of the analyte, a receptor binding the analog and the analyte, and a substrate upon which spots of liquid can spread.

The invention can best be understood with reference to the accompanying drawings and in the following detailed description of the preferred embodiments.

DESCRIPTION OF THE PREFERRED EMBODIMENTS

Figure 1:
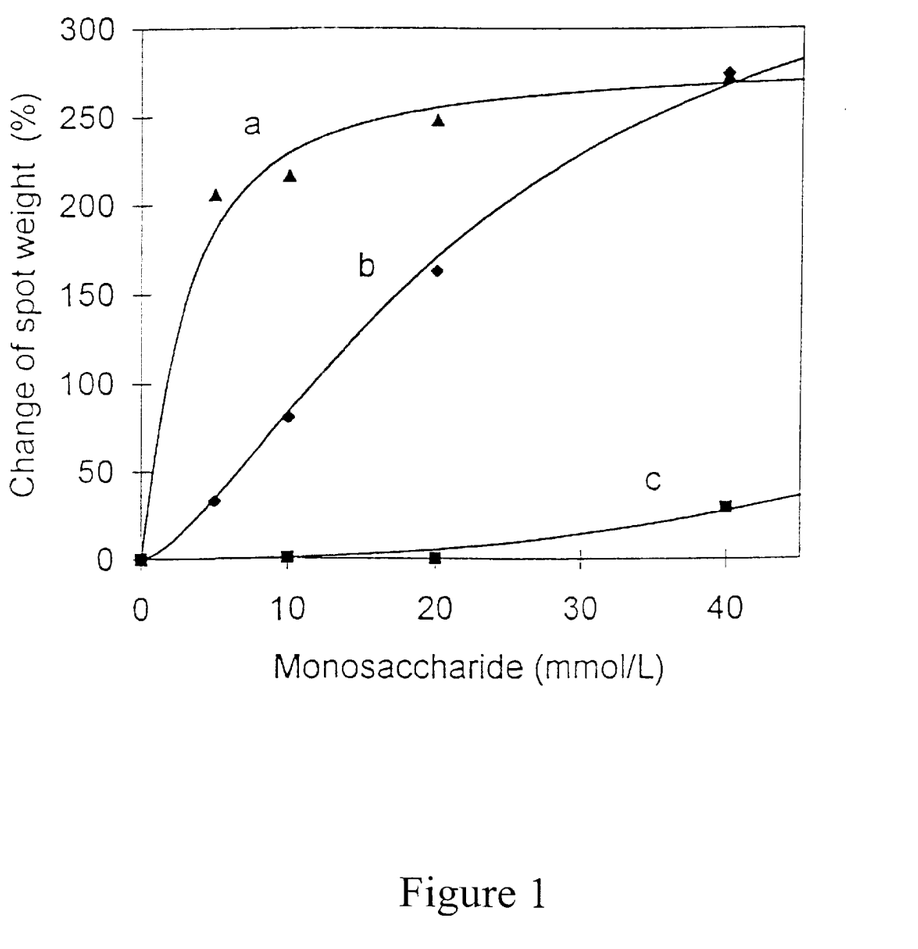
FIG. 1 graphically represents measurements of the change in spot weight for the various concentrations of three sugars using a dextran/Con-A dispersion.
Figure 2:
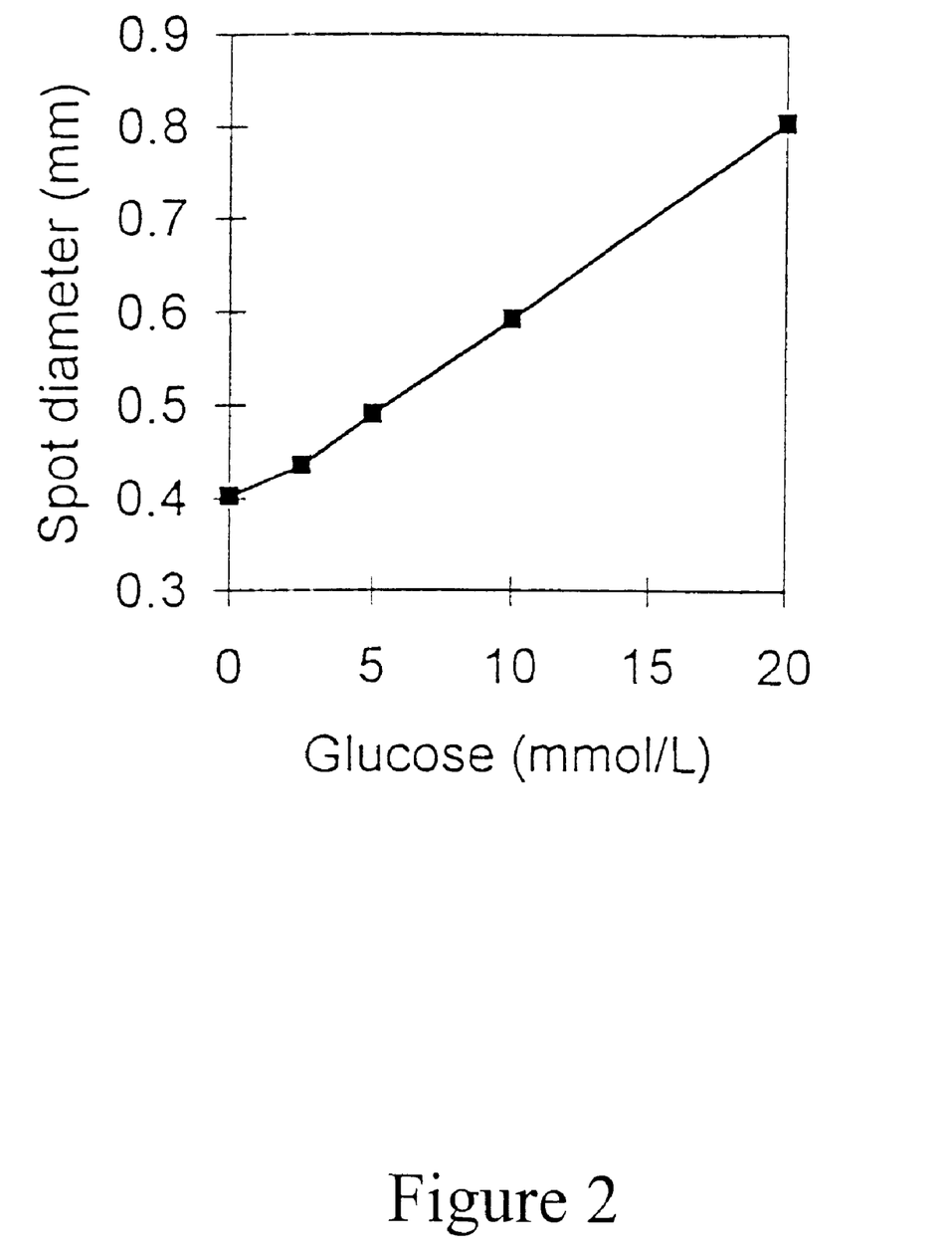
FIG. 2 is a graph representing the spot diameter plotted against glucose concentration of calf plasma.

The present invention provides a method of detecting the presence of an analyte in a test solution. The method utilizes a dispersion of a conjugate and a receptor.

The method can detect the presence of any solvable analyte in a solution, and the method also can detect the presence of analyte species in a dispersion. Thus, for example, the method can detect the presence of organic compounds such as sugars (e.g., glucose, mannose, galactose, etc.), proteins (e.g., serum proteins, antibodies, etc.), lipids, nucleic acids, natural or artificial polymers, pharmacologically active agents (e.g., toxins, drugs, hormones, etc.), industrial chemicals (e.g., desired reaction products, byproducts, waste products, etc.), organometallic compounds, organic nitrates, etc. Of course, an analyte can be an inorganic compound as well, and the inventive method can even detect the presence of large analytes (e.g., bacteria, viruses, prions, etc.). In some applications, an analyte detectable via the inventive method can be a species (e.g., lipids generally, or gram-positive bacteria generally, etc.). Conversely, in other applications, the inventive method can distinguish an analyte from other similar substances (e.g., glucose vis-à-vis mannose, one bacterial strain from another, one type of lipid from others, etc.).

The conjugate is any soluble species or any species able to form an aqueous dispersion, and which contains a ligand that selectively binds the receptor. By "selectively binds," it is meant that the ligand is bound with greater affinity in comparison with another species. Preferably, the conjugate is multivalent (having more than one ligand binding the receptor). The conjugate is desirably a polymeric species, such as, for example, a polysaccharide (e.g., containing mannose or glucose residues). A preferred polysaccharide conjugate is a dextran. However, the conjugate can be a polyamino acid or other polymer, provided the receptor can interact with the conjugate. The conjugate can be coupled with (e.g., covalently bonded to) a marker species, such as a dye, fluorescent moiety, or other similar substance to enhance the ability to visualize the presence of the conjugate.

The receptor is any species able to interact with the conjugate, as well as the analyte of interest, by forming high affinity bonds. To effect a viscosity change in the presence of the conjugate or the analyte, the receptor molecules should be multivalent (i.e., having at least two moieties for forming high affinity bonds with the analyte and/or the conjugate). Where the conjugate is a polysaccharide, a suitable receptor is a lectin, such as, for example, concanavalin A (Con-A), which has two to four mannose or glucose binding sites. However, the receptor can be another type of species able to form a high affinity bond with the conjugate, such as an antibody molecule or other similar receptor molecule. The receptor can be coupled with a marker species, such as a dye, fluorescent moiety, or other similar substance to enhance the ability to visualize the presence of the receptor.

The inventive method involves mixing the receptor and conjugate together to form a solution or an aqueous dispersion. Due to the high affinity interaction between the receptor and the conjugate mentioned above, the receptor and the conjugate cross-link within the dispersion. In some embodiments, when enough of the receptor and conjugate are present (at overlapping concentration of conjugate, about 1 v/v % for 2,000 kDa dextran), the cross-linking becomes extensive enough to alter the viscosity of the fluid. Preferably, the conjugate should be present in a sufficient concentration such that, in the presence of the receptor, the viscosity of the dispersion is greatly increased, most preferably by several orders of magnitude.

While the amount of conjugate necessary for this increase in viscosity depends on the type of conjugate and the type of receptor, where dextran and Con-A are employed, the dextran concentration required to effect the viscosity increase is between about 1 w/v % and about 10 w/v %. Preferably, the molecular weight of the dextran is above about 1000 kDa, and most preferably the dextran employed in the context of the present invention is dextran with a molecular weight of about 2000 kDa. Similarly, the amount of receptor necessary for the increase in viscosity depends on the type of conjugate and the type of receptor. However, where dextran and Con-A are employed, the Con-A concentration required to effect the viscosity increase is between about 0.4 w/v % and about 3 w/v % (e.g., between about 1 w/v % and about 2 w/v %).

As mentioned, the interaction between the receptor and the conjugate effects an increase in the viscosity of a dispersion containing the conjugate and the receptor. Importantly, however, the receptor for the conjugate also interacts with the analyte to be detected. Thus, the ligands on the conjugate are analogs of the analyte. Because the receptor is able to selectively bind the analyte, the analyte competes with the conjugate to bind the receptor, thereby interfering with the receptor-conjugate interaction. Thus, when an amount of the analyte is added to the dispersion containing the conjugate and the receptor, the viscosity of the dispersion is altered. The nature of the viscosity change upon addition of the analyte depends to a large extent on the nature of the analyte and the conjugate. For example, where the conjugate is a polymeric species, such as those described herein, and the analyte is not extensively crosslinked, the addition of the analyte will reduce the viscosity of the dispersion containing the conjugate and the receptor. However, where the analyte is itself a crosslinked species, it is possible that its addition will increase the viscosity of the dispersion containing the conjugate and the receptor. The probability of interference in the inventive method by non-specific interactions (e.g., by increased salt concentration or similar interference) is quite low because the viscosity change due to the specific interaction of the receptor with the conjugate and analyte is high.

To detect the presence of the analyte, thus, a quantity of the solution containing an unknown concentration of the analyte (the test solution) is introduced into an aliquot of the dispersion. Thereafter, the presence of analyte in the test solution is detected by noting a change in the viscosity of the dispersion. In the inventive method, viscosity is determined by measuring the ability of a drop of the dispersion to spread over the surface of a substrate. Spots of the dispersion and the aliquot containing the test solution within the dispersion are placed on a substrate. While, strictly speaking, the spots can be of different volumes, it is preferred that they be equivalent spots (i.e., spots of substantially equivalent volumes) to reduce or eliminate the effect of differential fluid volume on the spread of the spots on the substrate. Thus, preferably, the degree to which the spots spread over the substrate is primarily (and preferably substantially) controlled by the viscosity of the fluid forming the spots. More viscous fluids (i.e., those with a lesser concentration of analyte) produce smaller spots than less viscous solutions (i.e., those with a greater concentration of analyte). Consequently, the concentration of the analyte is related to the area of the spot. Thus, the presence of analyte in the test solution will be revealed if the area of the spot produced by the dispersion containing test solution differs from the area of the spot produced by the dispersion alone (i.e., the control solution).

The substrate can be any suitable material permitting spots of fluid to spread. Preferably, however, the substrate is formed from a hydrophilic, non-charged material such that the major factor influencing the rate of the dispersion is the viscosity of the fluid. Thus, the substrate can be formed from material such as cellulose-based paper. However, to promote even spread of the spots upon the substrate, preferably the substrate has a relatively even or uniform surface, such as, for example, that possessed by microcrystalline cellulose (e.g., that is normally employed in thin film chromatography applications).

In application, the inventive method functions best when the dynamic measuring range is high. The dynamic measuring range depends on the species of conjugate and receptor used in a given protocol. The sensitivity range and the signal dynamics of the analyte measurements can be modified by varying the concentration of the conjugate and/or the receptor. For example, because the viscosity is a logarithmic function of receptor concentration due to affinity interactions, when only the receptor concentration is raised, the viscosity is dramatically increased. However, when the conjugate concentration is raised, the sensitivity range is broadened, due chiefly to the added concentration of ligand moieties. Thus, a greater analyte concentration is required to disrupt the receptor/conjugate crosslinks. Of course, where the concentration of both the receptor and the conjugate is increased, both the sensitivity as well as the signal dynamics are affected. Where dextran and Con-A are employed, a low concentration of Dextran 2000 ™ (e.g., about 1 v/v %) and a relatively high concentration of Con-A (e.g., about 2.2 v/v %) can provide an increase in spot diameter by 100% in a range of glucose from 0 mM to about 20 mM.

Because the inventive method involves competition between the analyte and the conjugate for affinity-binding of the receptor, at some concentration (depending on other parameters of the system) the analyte concentration will saturate the receptor, resulting in little or no appreciable increase in spot size in response to a further increase in analyte concentration. The receptor is saturated at lower analyte concentrations if it has a significantly higher affinity for the analyte than for the conjugate. In this respect, it is desirable, under some conditions, to produce a concentration curve to optimize the concentrations and ratio of conjugate to receptor to achieve an approximately linear relationship between the analyte concentration and the spot size. Where an approximately linear relationship is established for a given analyte concentration in a given receptor/conjugate pair, only one control solution need be employed in a given assay to measure the concentration of analyte in the test solution.

To calibrate concentration, a solution containing a known quantity of the analyte is mixed into at least one aliquot of the dispersion (the control solution), as discussed above. Preferably, several aliquots of the dispersion are likewise diluted with different concentrations of the analyte to provide several points of reference (i.e., to create serial dilutions). When equivalent spots of such serial dilutions are placed on the substrate, as described, a gradient of spot sizes will result, which can be plotted as a concentration curve.

By developing a concentration curve, the system can be employed to measure the concentration of the analyte in the test solution, rather than merely to detect its presence. To thus measure concentration, equivalent spots of the dispersions (or solutions) containing known concentrations of analyte (which can include the control dispersion without any analyte, if desired) and the test dispersion (i.e., containing the unknown concentration of analyte) are placed on the substrate as described. After the spots have spread, the areas of all spots are compared to provide an indication of the concentration of the analyte in the test solution.

Employing such serial dilutions of analyte concentrations while varying conjugate and/or receptor concentration also can shift, in some systems, the range at which the system is most sensitive to changes in analyte concentration. For example, in applications in which the mere presence of an analyte in a test solution is assayed, preferably the system is adjusted so that very small amounts of analyte produce obvious changes in spot size. Conversely, the system can be rendered sensitive to analyte concentrations above a given threshold by adjusting the system to be less sensitive to the analyte concentration.

Because temperature and humidity will have an effect on the ability of a spot of some dispersions (e.g., aqueous dispersions) to spread over the surface of a substrate, it is important to calibrate the assay. If the assay is to be conducted under a standard test condition, a single calibration is required, using the same stocks of reagents. However, for field use, it is generally preferred to run control samples at the same time each test sample is assayed, as field conditions can vary considerably.

While the assay can be conducted until the spots dry, it also is possible to assess the area of the spots at a given time while they are still spreading (e.g., after about five minutes), so long as all control spots (i.e., the spots formed from the control solutions) and the test spot (i.e., the spot formed from the test solution) are assayed at about the same time. Once a spot has spread for the desired period of time, its area can be measured by any suitable method. For example, a spot can be excised from the substrate and weighed, or it can be scanned into a computer for electronic analysis of the area. Where the substrate is even-textured (such as those substrates discussed above), the drops typically will spread evenly to form substantially circular spots, which can be accurately sized by measuring diameter. A measurement of diameter can be more accurate than weighing samples, and such measurements are easier to conduct in the field (where complicated and sensitive balances and/or computerized equipment might be expensive or unavailable).

Another option to measure the analyte-induced viscosity change is by using fairly narrow (e.g., between about 1 mm and about 5 mm, typically about 2 mm) paper strips. A drop of dispersion is placed at the end of such a strip such that its expansion proceeds unidirectionally towards the dry end of the strip. The length of the band representing the drop spread correlates to analyte concentration as described above.

As mentioned, in some applications, it is possible to adjust the system to achieve an approximately linear relationship between analyte concentration and spot size, at least over a given concentration range. It is not necessary to achieve such a linear relationship; however, when the response is approximately linear, and when standard samples are employed, a fairly accurate approximation of the analyte concentration of an unknown sample can be achieved through mere visual comparison (i.e., without plotting concentration curves). This, of course, is desirable under field conditions and to minimize the necessity to employ expensive equipment. Moreover, as mentioned, the conjugate can be coupled to a marker species, such as a dye, fluorescent moiety, or other similar substance. Indeed, such a substance can be otherwise present in the drops containing the analyte and the dispersion. The presence of such a marker species facilitates the detection of the spots under certain circumstances. For example, where the drops contain a fluorescent moiety, resultant spots can be detected by causing the spots to fluoresce.

To effectuate the above-described method for detecting the presence of an analyte, the present invention provides a test kit suitable for detecting the presence of an analyte. The test kit includes, at a minimum, a conjugate (such as those set forth above) comprising an analog of the analyte, a receptor (such as those set forth above) binding the conjugate and the analyte, and a substrate (such as those set forth above) upon which spots of liquid can spread. The kit also can be employed to detect the concentration of the analyte. For such concentration measurements, the kit can include at least one solution containing a known concentration of the analyte for facilitating the calculation of a concentration curve, as discussed above. Alternatively, where the kit is to be employed under standard environmental conditions, its concentration sensitivity can be precalibrated.

The test kit can be constructed in any fashion. Preferably, the kit is sized to be readily portable for facilitating field use. Also, for ease of use, preferably, the kit includes a housing for supporting the substrate. The housing can completely enclose the substrate (e.g., as a box) to minimize the effect of variant atmospheric conditions on the assay. Preferably, the test kit includes a means for measuring the areas of spots on the substrate. Such a means can be, for example, a ruler or caliper device for measuring the diameter of the spots, a device (e.g., a scale) for weighing the spots, a device for scanning digital images of the spots for instant or later assessment of relative spot size, or other similar means. As mentioned, preferably the substrate used in the inventive method (and thus also in the test kit) has a relatively uniform surface, such as, for example microcrystalline cellulose. As such a substrate permits relatively even spread of the spots, where such a substrate is employed in the kit, the preferred means for measuring the area of spots is a ruler or caliper device able to measure the diameter of the spots. Such a device can be a separate instrument or can be included as part of the kit (e.g., as part of the housing of the kit). For example, one surface of the kit facing the support for the substrate can form a window for viewing the substrate. Such a window can have calibrations printed thereon for direct assessment or approximation of the area of spots formed on the substrate.

Where the conjugate and/or receptor is conjugated to a dye or a fluorescent moiety, the kit can comprise a means for detecting the dye or fluorescence (e.g., a colored window, an infrared or ultraviolet light source, etc.).

The following examples further illustrate the present invention. These examples are included here solely for illustrative purposes; accordingly, they should not be construed as in any way limiting the scope of the present invention.

Example 1

This example demonstrates the relationship between the area of a test spot and the concentration of analyte amidst a dispersion containing a receptor for the analyte and a conjugate.

A dispersion of 5 wt. % Dextran 2000 ™ (the conjugate) and 1 wt. % Con-A (the receptor) in phosphate buffered saline (PBS) (0.01 M PO$_4^{2-}$, pH 7.1) was first produced. Solutions containing 5 mM, 10 mM, 20 mM, and 40 mM glucose (the analyte) in PBS were also created.

Aliquots of 5 µl of each of the glucose solutions, and a 5 µl PBS aliquot containing no glucose, were introduced into 100 µl aliquots of the dextran/Con-A. The dispersions were carefully mixed at room temperature so as to avoid the creation of air bubbles. After mixing, 10 µl from each of the mixed glucose/Con-A/dextran dispersions were placed onto ordinary cellulose filter paper using a micropipette. Three spots from each sample were placed on the filter paper, sufficiently far apart to avoid contact as the drops spread. After 15 minutes, the spots had spread and dried.

The drops of each of the mixed glucose/Con-A/dextran dispersions spread unevenly on the filter paper. Greater analyte concentration resulted in less viscous dispersions and, consequently, larger spots.

Example 2

This example demonstrates that the relationship between the area of a test spot and the concentration of analyte amidst a dispersion containing a receptor for the analyte and a conjugate depends on the specific interaction between the analyte and the receptor.

A dextran/Con-A dispersion and glucose solutions were prepared as recited in Example 1. Additionally, solutions containing 5 mM, 10 mM, 20 mM, and 40 mM mannose and galactose, separately, in PBS were also created. Aliquots of each of the sugar solutions (and an aliquot of PBS) were mixed with aliquots of the dispersion as discussed above. 10 μl spots of each of the dispersion/sugar mixtures were placed on cellulose filter paper as described above.

After 15 minutes, the spots had spread and dried on the filter paper, forming irregular spots on the filter paper. To quantify the relationship between the area of the spots and the concentration of sugar introduced into the dispersion, the dried spots were physically excised from the paper and weighed. The spots were weighed singly, and a standard deviation was calculated as 10%. The spot weights for the various concentrations of each sugar were plotted in FIG. 1.

From these values, curves were plotted using the following equation:

$$A=(B*C^D)/(E+C^D)$$

where:

A= change in spot size (weight)

B= the maximum spot size

C= the monosaccharide concentration

D= slope of the graph

E= half-saturation concentration

The data reveal that, for the dextran/Con-A system, the glucose curve (i.e., curve "b" in FIG. 1) exhibits a near linear relationship between concentration and spot size within the tested concentrations. In contrast, for the dextran/con-A system, the mannose curve (i.e., curve "a" in FIG. 1) exhibits a sharp increase in spot size in response to relatively small changes in mannose concentration below about 5 mM, followed by substantially no changes in spot size with further increases in mannose concentration. This lower saturation value of mannose is consistent with the much higher affinity of Con-A for mannose residues than for glucose.

Data obtained for galactose reveal that over the range of 0 mM to 20 mM, spot size did not change substantially. Only at 40 mM was a slight increase in spot size observed (see curve "c" in FIG. 1).

As demonstrated, when Con-A is used as the receptor, the system best detects glucose-type sugars within the concentration ranges employed. This result demonstrates that the sensitivity of the system can be optimized relative to different analyets and concentrations.

Example 3

This example demonstrates the relationship between the area of a test spot and the concentration of analyte amidst a dispersion containing a receptor for the analyte and a conjugate.

Dispersions of Con-A and dextran, as well as serial dilutions of glucose solutions, were prepared essentially as indicated in Example 1. However, rhodamine-conjugated dextran was used in this example to permit detection of the spots by fluorescence. Additionally, the dispersion comprised 2.2 wt. % Con-A and 1.3 wt. % rhodamine-conjugated Dextran 2000 ™.

Aliquots of the dispersion and glucose solutions were mixed substantially as described in Example 1. 10 μl of each were placed on a 160 μm thick sheet of microcrystalline cellulose paper. After 15 minutes, the spots had spread and dried.

Consistent with the data presented in Example 1, greater glucose concentration resulted in larger spots. However, the use of microcrystalline cellulose paper in this example produced even, round spots. Thus, unlike the uneven spots discussed in Example 1 the size of those produced on microcrystalline cellulose paper could be assessed by measuring the diameter of the spots, which is a more accurate measurement. Indeed, the standard deviation calculated from measurements of the on microcrystalline cellulose is 3–4%, while, as indicated, that calculated for spots weighed in Examples 1 and 2 was 10%.

Example 4

This example demonstrates that the inventive method can be employed to measure blood glucose concentration.

A dispersion of Con-A and rhodamine-conjugated dextran was prepared as described in Example 3. Dialyzed calf blood plasma samples were spiked with varying concentrations of glucose (0 mM to 20 mM). Aliquots of the spiked plasma were mixed with aliquots of the dispersions as described above. The concentration of the dispersion as well as the mixing ratio of the sample solution and dispersion were optimized to achieve a high dynamic change of the spot size at normal blood glucose concentration (roughly 5 mM).

Drops of 10 μl of each of the plasma/dispersion mixtures were placed on the microcrystalline cellulose paper as described in Example 3. After 15 minutes, the drops had spread and dried. The drops were scanned, and their diameters were measured using a computer-generated caliper. FIG. 2 is a graph representing the spot diameter plotted against the glucose concentration of the spiked plasma. As can be seen, a simple comparison of spot diameter is useful for measuring the concentration of blood glucose well within normal physiological parameters.

All of the references cited herein, including patents, patent applications, and publications, are hereby incorporated in their entireties by reference.

While this invention has been described with an emphasis upon preferred embodiments and on illustrative examples, it will be obvious to those of ordinary skill in the art that variations may be used and that it is intended that the invention may be practiced otherwise than as specifically described herein. Accordingly, this invention includes all modifications encompassed within the spirit and scope of the invention as defined by the following claims.

What is claimed is:

1. A method of detecting an analyte in a test solution, said method comprising:

(a) providing a liquid composition of a conjugate and a receptor, wherein said conjugate comprises an analog of said analyte, and said receptor interacts with said analyte and said analog, (b) introducing said test solution into an aliquot of said liquid composition to create a mixture of said liquid composition and said test solution and to leave a volume of said liquid composition unmixed with said test solution, (c) placing substantially equivalent volumes of said liquid composition and said mixture separately on a substrate such that said volumes spread upon said substrate to form spots, each having an area, and (d) comparing the relative areas of said spots to provide an indication of the presence or absence of said analyte in said test solution.

2. The method of claim 1 employed for measuring the concentration of said analyte in said test solution, further comprising the steps of:

(e) introducing a known quantity of said analyte into a second aliquot of said liquid composition to create a second mixture, (f) placing substantially equivalent volumes of said liquid composition and said mixtures on said substrate to form spots, each having an area, and (g) comparing the relative areas of all spots to provide an indication of the concentration of said analyte in said test solution.

3. The method of claim 2, further comprising:

(e) introducing multiple known quantities of said analyte into aliquots of said liquid composition to create serial dilution mixtures, (f) placing substantially equivalent volumes of said liquid composition and said mixtures on said substrate to form spots, each having an area, and (g) comparing the relative areas of all spots to provide an indication of the concentration of said analyte in said test solution.

4. The method of claim 1, wherein said conjugate is dextran.

5. The method of claim 4, wherein said dextran has a molecular weight of about 2000 kDa.

6. The method of claim 1, wherein said receptor is a lectin.

7. The method of claim 6, wherein said lectin is concanavalin A.

8. The method of claim 1, wherein said analyte is selected from the group consisting of glucose and mannose.

9. The method of claim 8, wherein said solution is a blood product.

10. The method of claim 1, wherein said receptor is an antibody.

* * * * *

UNITED STATES PATENT AND TRADEMARK OFFICE
CERTIFICATE OF CORRECTION

PATENT NO.   : 6,271,044 B1                                                  Page 1 of 1
DATED        : August 7, 2001
INVENTOR(S)  : Ralph Ballerstadt; Jerome S. Schultz It is certified that error appears in the above-identified patent and that said Letters Patent is hereby corrected as shown below:

<u>Column 1,</u>
Immediately following the invention's Title, please insert the following paragraph
-- STATEMENT AS TO RIGHTS TO INVENTIONS MADE UNDER FEDERALLY SPONSORED RESEARCH AND DEVELOPMENT
This invention was made in part with United States Government support under Grant Number EM08540 awarded by the National Institutes of Health. The United States Government may have certain rights in this invention. --

Signed and Sealed this

Twelfth Day of March, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.     : 6,271,044 B1
DATED          : August 7, 2001
INVENTOR(S)    : Ralph Ballerstadt and Jerome S. Schultz It is certified that error appears in the above-identified patent and that said Letters Patent is hereby corrected as shown below:

<u>Column 1,</u>
Line 5, please replace the entire paragraph titled "Statement as to Rights to Inventions Made Under Federally Sponsored Research and Development" with the following:

-- STATEMENT AS TO RIGHTS TO INVENTIONS MADE UNDER
   FEDERALLY SPONSORED RESEARCH AND DEVELOPMENT
  This invention was made in part with United States Government support under Grant Number GM08540 awarded by the National Institutes of Health. The United States Government may have certain rights in this invention. --

Signed and Sealed this

Twenty-third Day of September, 2003

JAMES E. ROGAN
*Director of the United States Patent and Trademark Office*